US011510896B2

(12) United States Patent
Rosa-Calatrava et al.

(10) Patent No.: US 11,510,896 B2
(45) Date of Patent: Nov. 29, 2022

(54) ANTIVIRAL COMPOSITIONS FOR THE TREATMENT OF INFECTIONS LINKED TO CORONAVIRUSES (71) Applicants: UNIVERSITE CLAUDE BERNARD LYON 1, Villeurbanne (FR); INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR)

(72) Inventors: Manuel Rosa-Calatrava, Lyons (FR); Olivier Terrier, Lyons (FR); Anaïs Proust, Lyons (FR); Vincent Moules, Belleville (FR)

(73) Assignees: UNIVERSITE CLAUDE BERNARD LYON 1, Villeurbanne (FR); INSTITUTE NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 24 days.

(21) Appl. No.: 16/340,346

(22) PCT Filed: Oct. 20, 2017

(86) PCT No.: PCT/FR2017/052889
§ 371 (c)(1),
(2) Date: Jun. 17, 2019

(87) PCT Pub. No.: WO2018/073549
PCT Pub. Date: Apr. 26, 2018

(65) Prior Publication Data
US 2019/0307722 A1    Oct. 10, 2019

(30) Foreign Application Priority Data

Oct. 21, 2016    (FR) ...................................... 1660223

(51) Int. Cl.
*A61K 31/353*    (2006.01)
*A61P 31/14*    (2006.01)
*A61K 9/00*    (2006.01)
*A61K 31/35*    (2006.01)
*A61K 31/4375*    (2006.01)
*A61K 31/7056*    (2006.01)
*A61K 38/21*    (2006.01)
*A61K 31/351*    (2006.01)
*A61K 31/352*    (2006.01)
*A61K 45/06*    (2006.01)

(52) U.S. Cl.
CPC ............ *A61K 31/353* (2013.01); *A61K 9/007* (2013.01); *A61K 31/35* (2013.01); *A61K 31/351* (2013.01); *A61K 31/352* (2013.01); *A61K 31/4375* (2013.01); *A61K 31/7056* (2013.01); *A61K 38/21* (2013.01); *A61K 45/06* (2013.01); *A61P 31/14* (2018.01)

(58) Field of Classification Search
CPC .............. A61K 2300/00; A61K 31/351; A61K 31/352; A61K 31/4375; A61K 31/7056; A61K 38/21; A61K 31/35; A61K 31/353; A61K 45/06; A61K 9/007; A61P 31/14
USPC .................................................. 514/280, 200
See application file for complete search history.

(56) References Cited

U.S. PATENT DOCUMENTS

| 3,995,027 A | 11/1976 | Gale et al. |
| 8,956,626 B2* | 2/2015 | Moules .................... A61P 31/16 424/202.1 |
| 9,381,238 B2* | 7/2016 | Terrier ...................... C12N 7/00 |
| 9,433,592 B2* | 9/2016 | Rosa-Calatrava ... A61K 31/215 |
| 10,144,917 B2* | 12/2018 | Rosa-Calatrava ...... A61P 31/12 |
| 2009/0014954 A1 | 6/2009 | Hsu et al. |
| 2011/0218241 A1 | 9/2011 | Preston et al. |
| 2013/0072513 A1 | 3/2013 | Colman |
| 2018/0004293 A1 | 1/2018 | Bella et al. |
| 2018/0042937 A1 | 2/2018 | Rosa-Calatrava et al. |

FOREIGN PATENT DOCUMENTS

| CN | 1089851 A | 7/1994 |
| CN | 101108200 A | 1/2008 |
| CN | 104225026 A | 12/2014 |
| FR | 3 049 861 A1 | 10/2017 |
| WO | 2002/009699 A1 | 2/2002 |
| WO | 2003/101479 A1 | 12/2003 |
| WO | 2004037237 A1 | 5/2004 |
| WO | 2008/063727 A2 | 5/2008 |

(Continued)

OTHER PUBLICATIONS

Deng et al.Journal of Virology Sep. 2014, 88 (20) 11886-11898; DOI: 10.1128/JVI.01528-14).*
Darryl Falzarano et al (Inhibition of novel β coronavirus replication by a combination of interferon-α2b and ribavirin. Sci Rep. 2013;3: 1686. doi:10.1038/srep01686).*
Modjarrad K. (Treatment strategies for Middle East respiratory syndrome coronavirus. J Virus Erad. 2016;2(1):1-4. doi: 10.1016/S2055-6640(20)30696-8. PMID: 26866060; PMCID: PMC4745090.).*

(Continued)

*Primary Examiner* — Sabiha N Qazi
(74) *Attorney, Agent, or Firm* — Arrigo, Lee, Guttman & Mouta-Bellum LLP (57) ABSTRACT The present invention relates to a pharmaceutical or veterinary composition for its use in preventing and/or treating a MERS-CoV (Middle-East Respiratory Syndrome) coronavirus infection, characterised in that it comprises, in a suitable pharmaceutical vehicle, at least one compound chosen from apigenin and berberine.

8 Claims, 3 Drawing Sheets (56) References Cited

FOREIGN PATENT DOCUMENTS

| WO | 20130185126 A1 | 12/2013 |
|---|---|---|
| WO | 2015157223 A1 | 10/2015 |
| WO | 20160013793 A1 | 1/2016 |

OTHER PUBLICATIONS

European Patent Office, English Translation of the International Search Report for PCT application No. PCT/FR2017/052889.
European Patent Office, English Translation of the Written Opinion for PCT application No. PCT/FR2017/052889.
De Wit E. et al., "SARS and MERS: recent insights into emerging coronaviruses", Nature Reviews Microbiology, vol. 14, pp. 523-534 (2016).
Dijkman R. et al., "Human coronaviruses 229E and NL63: close yet still so far", Journal Formos Medical Association vol. 08, pp. 270-279 (2009).
Dyall J., et al., "Repurposing of clinically developed drugs for treatment of Middle East respiratory syndrome coronavirus infection". Antimicrobial Agents Chemotherapy; Aug. 2014; vol. 58, No. 8: pp. 4885-4893.
Jaffar A. Al-Tawfiq et al., "Ribavirin and Interferon Therapy in Patients Infected with the Middle East Respiratory Syndrome Coronavirus: An Observational Study". International Journal of Infectious Diseases: IJID: Official Publication of the International Society for Infectious Diseases; Mar. 2014, vol. 20, pp. 42-46.
Josset L., et al., "Cell host response to infection with novel human coronavirus EMC predicts potential antivirals and important differences with SARS coronavirus". MBio. Apr. 30, 2013; vol. 4, issue 2, pp. 1-11.
Adedeji A.O., et al., "Antiviral drugs specific for coronaviruses in preclinical development". Curr Opin Virol., Oct. 2014; No. 8: pp. 45-53.
Kilianski A. et al., "Cell-based antiviral screening against coronaviruses: developing virus-specific and broad-spectrum inhibitors". Antiviral Research, Jan. 2014; No. 101: pp. 105-112.
Shibata C. et al., "The flavonoid apigenin inhibits hepatitis C virus replication by decreasing mature microRNA122 levels", Virology, Aug. 2014; Nos. 462-463: pp. 42-48.
Lv X., et al., "Apigenin inhibits enterovirus 71 replication through suppressing viral IRES activity and modulating cellular JNK pathway", Antiviral Research, Jun. 24, 2014; No. 109: pp. 30-41.
Song S., et al., "Berberine down-regulates cellular JNK and NF-κB activation and this may result in an inhibition of HSV replication". Antimicrobal Agents And Chemotherapy, Jun. 9, 2014., vol. 58, No. 9.: pp. 5068-5078.
Wu Y., et al., "In vivo and in vitro antiviral effects of berberine on influenza virus", Chinese Journal Integrated Medicine, Jun. 17, 2011 No. 6: pp. 444-452.
Falzarano D. et al., "Treatment with interferon-a2b and ribavirin improves outcome in MERS-CoV-infected rhesus macaques", Nature Medicine, Sep. 8, 2013, vol. 19, No. 10, pp. 1313-1317.
Young Bae Ryu et al., Bioflavinoids from Torreya nucifers displaying SARS-Cov 3CLpro inhibition, Bioorg. Med. Chem., 2010, vol. 18, p. 7940-7947.
Fang et al., J Int Pharm Res, vol. 37, No. 2, 2010, 105-113.
Nemann et al., Post-translational glycosylation of coronavirus glycoprotein E1: inhibition by monensin, The EMBO Journal vol. 1 No. 12 pp. 1499-1504, 1982.
Japanese Patent Office, Office Action in Japanese Application, 2019-521029, dated Jul. 12, 2021.

* cited by examiner

Figure 3

ANTIVIRAL COMPOSITIONS FOR THE TREATMENT OF INFECTIONS LINKED TO CORONAVIRUSES

The present invention relates to compositions for their use in treating MERS-CoV (Middle-East Respiratory Syndrome) coronavirus-related viral infections, in humans and animals.

The MERS-CoV coronavirus is a new emerging virus identified in 2012 in Saudi Arabia, responsible for severe acute respiratory syndrome and kidney failure. Since its identification, this virus has been responsible for more than 1806 infection cases in 26 countries, mainly in the Middle East. It is responsible for 643 deaths, that is close to 35.6% of mortality according to the World Health Organization (WHO Source, 28 Sep. 2016).

MERS-CoV belongs to the order Nidovirales, the family Coronaviridae, and the genus *Betacoronavirus*.

The coronaviruses are enveloped viruses, having a capside having a helical symmetry. They have a single-stranded positive sense RNA genome, and are capable of infecting cells from birds and mammals. The viruses which are members of this very wide family are known to be causative agents for cold (for example hCoV and OC43 viruses), bronchiolitis (for example NL63 virus) or even some forms of several *pneumoniae* as those observed during the SARS (such as the Severe Acute Respiratory Syndrome Coronavirus, SARS-CoV) epidemic.

Although they belong to a same viral family, significant differences exist between the different coronaviruses, both at the genetic and structural level, but also in terms of biology and sensitivity to antiviral molecules (see for reference Dijkman & van der Hoek 2009; de Wit et al., 2016).

Although most cases of MERS-CoV in humans are attributable to a human-to-human transmission, camels appear to be a permanent MERS-CoV infected intermediate animal host and thus make up the main infection animal source in humans.

To date, there is no prophylactic or therapeutic solution to efficiently treat this epidemic respiratory viral pathogen having a pandemic potential.

Several therapeutic pathways have been recently explored: use of ribavirin, interferon, or even mycophenolic acid. Unfortunately, most of these compounds have not shown a sufficient efficiency, when used in infected patients (Al-Tawfiq et al., 2014) or within the scope of a prophylactic treatment (de Wit et al., 2016).

A first strategy for identifying active compounds against MERS-CoV has been to test, among the numerous known antiviral molecules, those used to fight SARS-CoV. Thus, viral replication inhibitors, such as protease inhibitors, helicase inhibitors, and virus entry inhibitors in target cells have been tested in vitro (see for review Adedeji & Sarafianos, 2014, and Kilianski & Baker, 2014).

Dyall et al. (Dyall et al., 2014) have tested different categories of drugs for the purpose of identifying antiviral agents which are active on SARS and/or MERS-COV coronaviruses. Among the different agent classes tested, it has been shown that some anti-inflammatory agents inhibit SARS-CoV proliferation, whereas MERS-CoV is rather inhibited by some ion transport inhibitors, tubulin inhibitors, or apoptosis inhibitors. Out of the 290 compounds tested, only 33 compounds having an antiviral activity on MERS-CoV have been identified in cell culture.

However, numerous literature data indicate that the antiviral compounds which are efficient on SARS-CoV are not systematically active against MERS-CoV, and vice-versa; these viruses having differences in terms both of protein composition and functional interactions with the host cell. (Dijkman & van der Hoek 2009; Dyall et al., 2014).

An alternative strategy to identify new therapeutic molecules is to test molecules having an action on cell signalling, biogenesis and metabolic pathways that the viruses target and/or divert to their advantage to carry their replicative cycle through to a successful conclusion. This strategy, set out in the paper of Josset et al. (Plos One, 2010), has already enabled molecules having an antiviral activity against the influenza viruses to be identified, such as molecules set out in patent applications FR 2 953 410, FR 3 033 701 and FR 3 049 861.

On the other hand, Josset et al. have highlighted the fact that MERS-CoV induces a gene expression profile of the target cells it infects, which is quite different from that induced by SARS-CoV. According to this study, glucocorticoid and kinase inhibitors could be pharmaceutical classes to be favoured for the research for active antiviral compounds on the MERS-COV coronavirus. (Josset et al., 2013).

To date, there is no, or very little, therapeutic molecules recognised and/or approved by health authorities to fight MERS-CoV virus infections.

On the other hand, there is no vaccine against the MERS-CoV virus on the market. Some candidates are currently tested in phase I clinical trials (Phase I, Open Label Dose Ranging Safety Study of GLS-5300 in Healthy Volunteers—Full Text View—ClinicalTrials.gov," accessed Mar. 24, 2016, https://clinicaltrials.gov/ct2/show/NCT02670187?term=ME RS+coronavirus&rank=7).

Under these conditions, there is a need for new prophylactic and/or therapeutic solutions against MERS-CoV coronavirus infections.

SUMMARY OF THE INVENTION

Within the scope of the present invention, several compounds have been selected and tested in a viral infection cellular test. Thereby, some compounds had an unexpected antiviral effect on the MERS-CoV coronavirus.

The selected compounds had been described beforehand for other therapeutic applications. Surprisingly, it has now been shown that these compounds, alone or in combination, have an antiviral activity against MERS-CoV, and enable infections by this coronavirus to be treated and/or prevented.

The invention relates to pharmaceutical or veterinary compositions for their use in preventing and/or treating a MERS-CoV (Middle-East Respiratory Syndrome) coronavirus infection, characterised in that it comprises, in a suitable pharmaceutical vehicle, at least one compound chosen from Apigenin and Berberine.

The invention is also concerned with a pharmaceutical or veterinary composition for its use in preventing and/or treating a MERS-CoV (Middle-East Respiratory Syndrome) coronavirus infection, characterised in that it comprises, in a suitable pharmaceutical vehicle, at least one compound chosen from apigenin, berberine and monensin, or a combination of at least two of these compounds.

These pharmaceutical or veterinary compositions can advantageously further comprise at least another antiviral agent, and/or antibacterial agent. For the purposes of the invention, another antiviral agent is an agent distinct from apigenin, berberine and monensin. Also, for the purposes of the invention, an antibacterial agent is an agent distinct from apigenin, berberine and monensin.

Another object of the invention is also pharmaceutical or veterinary compositions comprising at least one antiviral agent in combination with at least one compound chosen from apigenin, berberine and monensin, or a combination of two of these compounds, or a combination of these three compounds.

In particular, said composition comprises in a suitable pharmaceutical vehicle, at least two compounds chosen from:
(a) an antiviral agent; and
(b) a compound chosen from apigenin, berberine, and a combination of both.

Another object of the invention is also pharmaceutical or veterinary compositions, comprising in a suitable pharmaceutical vehicle, a combination of berberine and monensin.

According to a particular aspect of the invention, said compositions are in a dosage form intended for administration by inhalation.

DETAILED DESCRIPTION OF THE INVENTION

The present invention relates to a pharmaceutical or veterinary composition for its use in preventing and/or treating a MERS-CoV (Middle-East Respiratory Syndrome) coronavirus infection, characterised in that it comprises, in a suitable pharmaceutical vehicle, at least one compound chosen from Apigenin and Berberine.

The compositions according to the invention are intended in particular for use in treating a MERS-CoV coronavirus infection.

By "MERS-CoV coronavirus infection", it is meant that a human or animal organism has cells that have been infected by the MERS-CoV coronavirus. The infection can in particular be established by performing a detection and/or viral titration from respiratory samples, or by assaying blood-circulating MERS-CoV-specific antibodies. The detection in the individuals infected with this specific virus is made by conventional diagnostic methods, in particular of molecular biology (PCR), which are well known to those skilled in the art.

The term "treatment/treating" designates fighting the MERS-CoV coronavirus infection in a human or animal organism. By virtue of the administration of at least one composition according to the invention, the viral infection rate (infectious titre) in the organism will decrease, and preferably the virus will completely disappear from the organism. The term "treatment treating" also designates attenuating symptoms associated with the viral infection (respiratory syndrome, kidney failure, fever, etc. . . . ).

The compositions according to the invention are also intended to be used in preventing a MERS-CoV infection.

For the purposes of the invention, the term "prevention/preventing" designates stopping, or at least decreasing the probability of occurrence of an infection in a human or animal organism by the MERS-CoV. By virtue of the administration of at least one composition according to the invention, the human or animal cells of said organism become less permissive to the infection, and are thus more likely not to be infected with said coronavirus.

The compositions according to the invention can be of the pharmaceutical type, intended to be administrated to a human being, or of the veterinary type, intended to be administrated to non-human animals.

As regards animals, it is understood that the veterinary compositions for their use in preventing and/or treating a MERS-CoV (Middle-East Respiratory Syndrome) coronavirus infection are intended to be administrated to animals infected with this coronavirus. These compositions are in particular intended to mammals, in particular commercial animals, and in particular mammals from the family camelidae and quite particularly to camels (genus *Camelus*).

According to the invention, the term "suitable pharmaceutical vehicle" designates vehicles or excipients, that is compounds having no action peculiar to the infection considered herein. These vehicles or excipients are pharmaceutically acceptable, which means that they can be administrated to an individual or animal without generating significant deleterious effects.

According to a first aspect, the pharmaceutical or veterinary composition for its use according to the invention comprises at least one efficient amount of apigenin.

According to a second aspect, the pharmaceutical or veterinary composition for its use according to the invention comprises at least one efficient amount of berberine.

By "efficient amount", it is meant for the purposes of the invention an amount of active compound sufficient to inhibit the proliferation and/or replication of the coronavirus, and/or the development of the viral infection within the organism. This inhibition can be quantised, for example by measuring the viral titre as is exhibited in the examples of the present application.

According to a preferred aspect of the invention, said pharmaceutical or veterinary composition for its use as mentioned before is characterised in that it comprises a combination of at least two of the following compounds: apigenin, berberine and monensin.

Said pharmaceutical composition could in particular comprise one of the following combinations:
Apigenin and Berberine;
Apigenin and Monensin;
Berberine and Monensin; or
Apigenin, Berberine and Monensin.

According to a particular aspect of the invention, the pharmaceutical composition for its use according to the invention will consist of one of the combinations of compounds as mentioned above, and an adapted pharmaceutical vehicle.

These compounds are known for use in other therapeutic applications largely irrelevant to an antiviral activity against the MERS-CoV coronavirus, as is set forth below.

Apigenin

Apigenin is a natural compound from the flavone family (flavonoids), found in parsley, plantain, milfoil, passion flower or even rosemary.

Its structural chemical formula is depicted below:

Formula I

This molecule is known for its anti-inflammatory properties, even if its mode of action is not known in detail. Some works indicate that apigenin acts by inhibiting cytochrome P450.

Apigenin has shown its efficiency against some viruses, such as HVC (hepatitis C virus) (Shibata et al. 2014), enterovirus 71 (Lv et al. 2014) or even gamma herpes virus (WO 2016/013793).

Berberine

Berberine is a natural alkaloid found in many plants.

Its structural chemical formula is depicted below:

Formula II

This molecule is widely used in the Asia pharmacopeia, for its antifungal, antibacterial and anti-inflammatory properties.

Its mechanism of action, although not completely elucidated, would substantially relate to AMP Kinase (Adenosine Monophosphate activated Protein Kinase) activation. This ubiquitous enzyme plays a role in cell energy homeostasis. The AMPK activation mainly results in (i) stimulating liver fatty acids and ketogenesis, (ii) inhibiting cholesterol synthesis, triglyceride lipogenesis and synthesis, (iii) stimulating the fatty acid oxidation in skeleton muscles and muscle glucose uptake, and (iv) modulating insulin secretion by pancreas beta cells.

Berberine has an antiviral activity on the HSV virus (Song et al. 2014) and on influenza viruses (Wu et al. 2011).

Furthermore, berberine could have an antiviral action against SARS-CoV (http://apps.who.int/medicinedocs/fr/d/Js6170e/ and WO 2013/185126), although no experimental data is available.

Monensin

Monensin is a polyether antibiotic isolated in a bacterium from the genus *Streptomyces*. This molecule is very widely used as an additive in ruminant feed (as the trade name Rumensin®), to prevent coccidiosis type infections.

Its structural chemical formula is depicted below:

Monensin would act as an ionophore, by disturbing the intracellular traffic.

This molecule is known to have a significant cytotoxicity when used at high concentrations. In animals, very significant differences of LD50 (Lethal dose 50%) exist. For example, in horses, the LD50 is 100 times less than in ruminants, which rises very high feed cross contamination intoxication problems in some farms.

An increasing number of literature data also shows an anti-malarial activity, as well as an antiviral activity against several viruses: against the influenza viruses (FR 3 033 701 and FR 3 049 861) and more particularly against enveloped viruses, including some viruses which are members of the coronavirus family.

Patent application US 2009/0149545 mentions many compounds, in particular monensin, for its therapeutic action against coronavirus infection.

Patent application WO 2015/157223, relating to the research for compounds having an antiviral activity against coronaviruses, reports that monensin could be used against the MERS-CoV, however without having experimental results enabling to draw this conclusion.

Antiviral Agent

For the purposes of the present invention, by the terms "antiviral agent" or "antiviral compound" it is meant active agents which act on the viral load (also called infectious titre), by inhibiting either directly or indirectly the replication and/or dissemination of the MERS-CoV coronavirus infection, within an infected organism.

By "antiviral activity" or "antiviral action", it is meant an action on the virus or on its target cells, in particular the action of inhibiting the replication cycle of the virus or its ability to infect and to be reproduced in host cells, wherein this antiviral effect can be obtained by modulating a number of genes of the target cells.

By "target cells", it is meant cells infected with the coronavirus and/or likely to be infected in the near future, because of their close proximity with infected cells.

Combination with Another Active Agent

It is understood that the composition for its use according to the invention comprises apigenin and/or berberine, and that it can also comprise other active compounds, in addition to the suitable pharmaceutical vehicle.

Indeed, apigenin, berberine and monensin, or mixtures thereof, can be employed in therapy alone, or in combination with at least another active agent.

It can be compounds enabling the activity of these compounds to be improved, or even other active agents known for a particular activity.

These further active compounds could be chosen from the pharmaceutical classes of agents mentioned in application WO 2015/157223, namely from the antibacterial agents, antiparasitic agents, neurotransmission inhibitors, estrogen receptor inhibitors, DNA synthesis and replication inhibitors, protein maturation inhibitors, kinase pathway inhibitors, cytoskeleton inhibitors, lipid metabolism inhibitors, anti-inflammatory agents, ion channel inhibitors, apoptosis inhibitors and cathepsin inhibitors.

These active compounds could be chosen in particular from antibacterial agents, ion channel inhibitors, immunosuppressive agents and antiviral agents. As an antiviral agent, acyclovir can in particular be mentioned.

According to a particular aspect of the invention, the pharmaceutical or veterinary composition for its use in preventing and/or treating a MERS-CoV coronavirus infection, comprises, in addition to apigenin and/or berberine, at least another antiviral agent.

According to another particular aspect of the invention, the pharmaceutical or veterinary composition for its use in preventing and/or treating a MERS-CoV coronavirus infection, comprises, in addition to a combination of at least two compounds chosen from apigenin, berberine and monensin, at least another antiviral agent.

It is understood that this antiviral agent will be used at doses necessary to have an antiviral action, this dose being designated as being "efficient", this dosage being possibly readily determined by those skilled in the art.

For the purposes of the invention, an antiviral agent designates a compound acting on a virus, by inhibiting and/or slowing and/or preventing the associated viral infection.

Antiviral agents are classified in different categories depending on their mode of action. These include in particular:
- nucleotide analogues, which interfere or stop DNA or RNA synthesis; as well as inhibitors of the enzymes involved in DNA or RNA synthesis (helicase, replicase);
- compounds which inhibit the virus maturation steps during its replication cycle;
- compounds which interfere with cell membrane binding, or virus entry in host cells (fusion or entry inhibitors);
- agents which prevent the virus from being expressed within the host cell after its entry, by blocking its disassembly within the cell;
- agents which restrict virus propagation to other cells.

One can mention in particular antiviral agents well known to those skilled in the art, intended to fight RNA viruses, such as protease inhibitors, helicase inhibitors, and MERS-CoV virus cell entry inhibitors in target cells.

Among the antiviral agents well known to those skilled in the art, one can mention more precisely ribavirin, a guanosine nucleoside analogue with a wide antiviral spectrum; as well as the interferon which acts by inhibiting the viral replication in the host cells.

According to a particular aspect of the invention, the pharmaceutical or veterinary composition is characterised in that the other antiviral agent is chosen from the following compounds: ribavirin, an interferon, or a combination of both.

For the purposes of the invention, by "an interferon" or "the interferon", it is meant a compound belonging to the interferon family, which are glycoproteins secreted by the cells of the immune system.

The interferons are a family of small protein molecules with a molecular weight of about 15 000 to 21 000 Daltons. Three major interferon classes have been identified: alpha, beta and gamma. These 3 main classes are not homogenous themselves and can gather several different interferon molecular species. More than 14 genetically different human alpha interferons have been identified.

It is understood that in the pharmaceutical or veterinary composition according to the invention, the interferon which is used will be a recombinant polypeptide, synthesised in laboratory.

In particular, the interferon which is used will be recombinant interferon alpha-2b the efficiency of which on the in vivo and in vitro viral replication has been demonstrated.

Such antiviral agents are commercially available, and their conditions of use are described in reference books such as Le Dictionnaire Vidal.

Thus, the pharmaceutical composition for its use according to the invention could comprise one of the following combinations:
- Apigenin, berberine and ribavirin;
- Apigenin, berberine and interferon;
- Apigenin, berberine, interferon and ribavirin;
- Apigenin, monensin and ribavirin;
- Apigenin, monensin and interferon;
- Apigenin, monensin, interferon and ribavirin;
- Berberine, monensin and ribavirin;
- Berberine, monensin and interferon;
- Berberine, monensin, interferon and ribavirin;
- Apigenin, berberine, monensin and ribavirin;
- Apigenin, berberine, monensin and interferon;
- Apigenin, berberine, monensin, interferon and ribavirin.

According to a particular aspect of the invention, the pharmaceutical composition for its use according to the invention will consist of a combination of active agents such as mentioned above, and an adapted pharmaceutical vehicle.

Mode of Administration of the Pharmaceutical or Veterinary Compositions

The pharmaceutical or veterinary compositions for use according to the present invention are adapted for an oral, sublingual, inhalation, subcutaneous, intramuscular, intravenous, transdermal, ocular or rectal administration.

According to a particular implementation of the invention, the pharmaceutical or veterinary composition for its use according to the invention is characterised in that it is in a dosage form intended for an administration by inhalation.

The inhalation designates the absorption by the airways. It is in particular a method of absorption of compounds for therapeutic purposes, of some substances as gas, microdroplets or suspended powder.

The administration of pharmaceutical or veterinary composition by inhalation, that is by the nasal and/or oral airways, is well known to those skilled in the art.

Two types of administration by inhalation are distinguished:
the administration by insufflation when the compositions are in the form of powders, and
the administration by nebulisation when the compositions are in the form of aerosols (suspensions) or in the form of solutions, for example aqueous pressurised solutions. The use of a nebuliser or a sprayer will be thereby recommended to administer the pharmaceutical or veterinary composition.

The dosage form considered here is thus chosen from: a powder, an aqueous solution of droplets or a pressurised solution.

Combination Product

The present invention also relates to a combination product comprising:
a composition according to the invention, comprising at least one compound chosen from apigenin and berberine, optionally in the presence of monensin, and
at least one antiviral agent,
for a simultaneous, separate or sequential use to prevent and/or treat a MERS-CoV coronavirus infection, in humans or animals.

Such a combination product could be used in preventing and/or treating a MERS-CoV coronavirus infection, within the scope of a simultaneous, separate or sequential use. Thus, the at least two active agents comprised in the combination product could be simultaneously, separately or sequentially administered.

It is understood that all combinations of two, three or four active compounds mentioned previously can each be in the form of a combination product, that is the two, three or four active compounds can be simultaneously, separately or sequentially administered, to prevent and/or treat a MERS-CoV coronavirus infection.

The invention also relates to a therapeutic method for preventing and/or treating a MERS-CoV coronavirus infection in humans, wherein an efficient amount of a compound chosen from apigenin and berberine, or a mixture of both, optionally in association with monensin is administered to a patient.

The invention also relates to a therapeutic method for preventing and/or treating a MERS-CoV coronavirus infection in animals, wherein an efficient amount of a compound chosen from apigenin and berberine, optionally in association with monensin is administered to an animal.

The invention also relates to the use of a compound chosen from apigenin and berberine, optionally in association with monensin, for preparing a pharmaceutical composition for preventing and/or treating a MERS-CoV coronavirus infection.

Pharmaceutical or Veterinary Compositions

The present invention also relates to a pharmaceutical or veterinary composition, comprising in a suitable pharmaceutical vehicle, at least two compounds chosen from:
(a) an antiviral agent; and
(b) a compound chosen from apigenin, berberine, and a combination of both.

In particular, the antiviral agent is intended for fighting a MERS coronavirus infection.

The viral agent could in particular be chosen from:
nucleotide analogues, which interfere or stop DNA or RNA synthesis; as well as inhibitors of the enzymes involved in DNA or RNA synthesis (helicase, replicase);
compounds which inhibit the virus maturation steps during its replication cycle;
compounds which interfere with cell membrane binding, or virus entry in host cells (fusion or entry inhibitors);
agents which prevent the virus from being expressed within the host cell after its entry, by blocking its disassembly within the cell;
agents which restrict virus propagation to other cells.

One can mention in particular antiviral agents well known to those skilled in the art, intended to fight RNA viruses, such as protease inhibitors, helicase inhibitors, and virus cell entry inhibitors in target cells.

Among the antiviral agents well known to those skilled in the art, one can mention more precisely ribavirin, a guanosine nucleoside analogue with a wide antiviral spectrum; as well as the interferon which acts by inhibiting the viral replication in the host cells.

According to a particular aspect of the invention, the composition contains, as an antiviral agent, an interferon, ribavirin, or a combination of both.

The pharmaceutical composition according to the invention could also comprise monensin.

Thus, the pharmaceutical composition according to the invention could comprise one of the following combinations:
Apigenin and ribavirin;
Apigenin and interferon;
Apigenin, interferon and ribavirin;
Berberine and ribavirin;
Berberine and interferon;
Berberine, interferon and ribavirin;
Apigenin, berberine and ribavirin;
Apigenin, berberine and interferon;
Apigenin, berberine, interferon and ribavirin;
Apigenin, monensin and ribavirin;
Apigenin, monensin and interferon;
Apigenin, monensin, interferon and ribavirin;
Berberine, monensin and ribavirin;
Berberine, monensin and interferon;
Berberine, monensin, interferon and ribavirin;
Apigenin, berberine, monensin and ribavirin;
Apigenin, berberine, monensin and interferon;
Apigenin, berberine, monensin, interferon and ribavirin.

According to a particular aspect of the invention, the pharmaceutical or veterinary composition according to the invention will consist of a combination of active agents as mentioned above, and an adapted pharmaceutical vehicle.

More particularly, the pharmaceutical or veterinary composition according to the invention will comprise, in a suitable pharmaceutical vehicle, at least one combination of an interferon, monensin, apigenin and berberine.

Such compositions could be used in any kind of therapeutic or prophylactic use, and will be in particular used in treating and/or preventing viral infections.

The compositions according to the invention can be of the pharmaceutical type intended to be administered to a human being, or of the veterinary type, intended to be administered to non-human animals.

As regards animals, the veterinary compositions according to the invention are in particular intended to mammals, in particular commercial animals, an in particular mammals of the family camelidae, and more particular to camels (genus *camelus*).

However, it is to be noted that monensin has a strong toxicity in horses (genus *Equus*) and that the veterinary compositions according to the invention comprising monensin are not intended for an administration to mammals belonging to the genus *Equus*.

Such compositions could in particular be used in treating and/or preventing coronavirus infections, and quite particularly by the MERS-CoV coronavirus infection.

According to a particular implementation of the invention, such compositions could be in a dosage form intended for an administration by inhalation.

Berberine and Monensin Combination

The present invention also relates to a pharmaceutical or veterinary composition, comprising in a suitable pharmaceutical vehicle, a combination of berberine and monensin.

Said composition could be used in any kind of therapeutic or prophylactic use, and will be in particular used in treating and/or preventing viral infections.

Such a composition comprising a combination of berberine and monensin could be used in particular in treating and/or preventing coronavirus infections, and quite particularly by the MERS-CoV coronavirus.

According to a particular implementation of the invention, this composition could be in a dosage form intended for an administration by inhalation.

Examples

The examples set out below demonstrate that the above-mentioned compounds unexpectedly have a significant antiviral activity to MERS-CoV, in vitro on two distinct mammal cell models, under moderate cytotoxicity conditions.

Firstly, the compounds have been tested in vitro, at a concentration conventionally used in literature, within the context of an infection of VERO-E6 cells by the MERS-CoV strain France-UAE/1612/2013, Genbank accession number KF745068.

The VERO-E6 cells come from monkey kidney epithelial cells, and are sensitive to MERS-CoV infection. They make up one of the study cellular models widely used in literature.

The infection parameters have been determined beforehand in order to obtain the best conditions to observe a possible antiviral effect.

The VERO-E6 cells have been infected at a MOI (Multiplicity Of Infection) of 0.5 for a duration of 24 h at 37° C. under 5% CO2, in the presence or absence of the tested compounds.

After a 24 h incubation, the infectious titres (log 10 DITC50/mL or DITC50/mL) have been determined in culture supernatants of infected cells.

Figure 1:
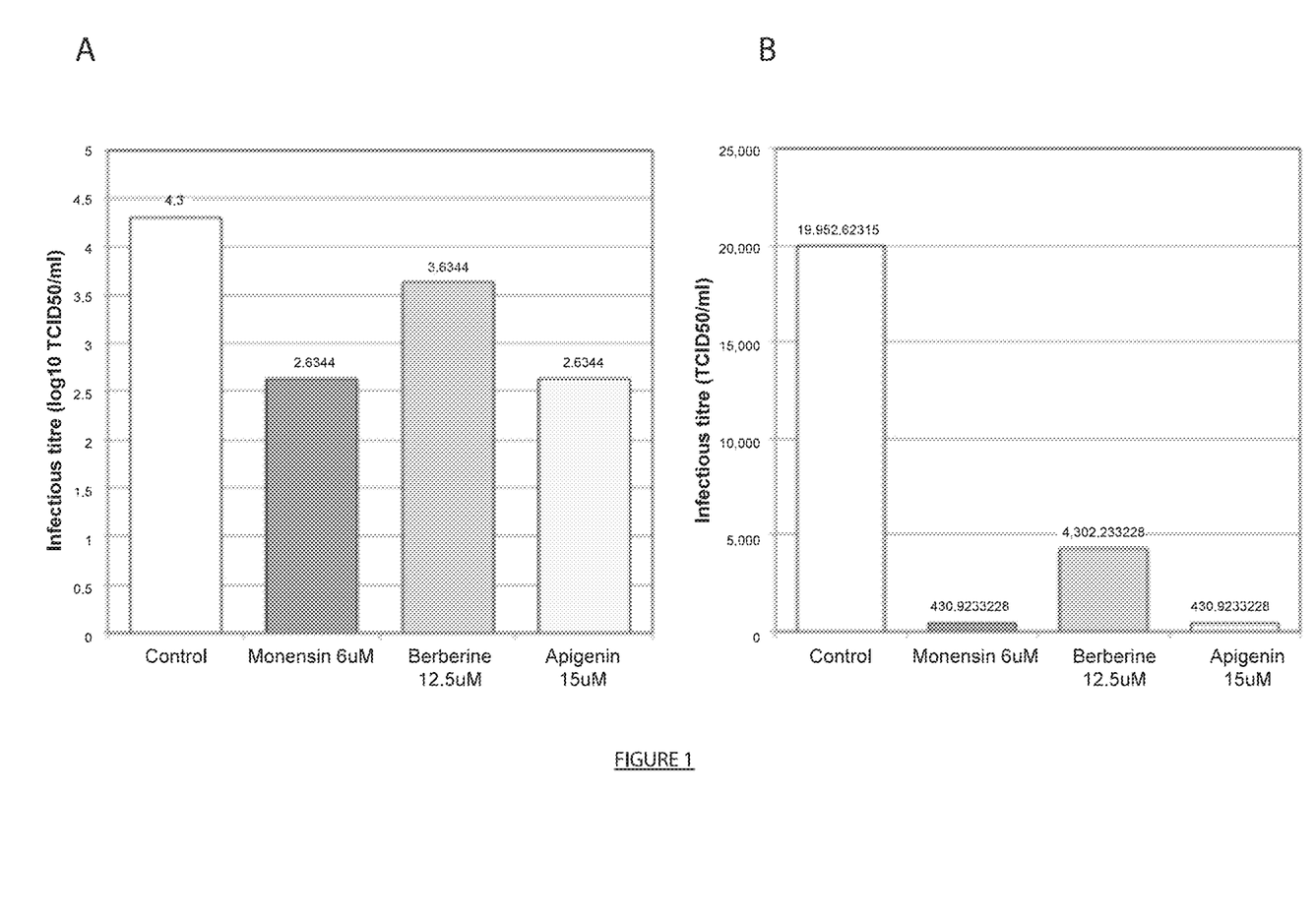
FIG. 1. Measurement MERS-CoV infectious titres of at 24 hours post-infection, on treated cells (by monensin, berberine or apigenin), relative to the infectious titre of the infected, not treated control cells. The infectious titres have been obtained by the limit dilution infection technique and calculation by the Reed and Muench method.
A) The results are expressed in log 10 TCID/mL (50% Tissue Culture Infective Dose)
B) The results are expressed in TCID/mL.

The infectious titres are indicated in TCID50/mL (50% Tissue Culture Infective Dose) in FIG. 1A (log 10 TCID50/mL) and FIG. 1B (TCID50/mL). They have been obtained by the limit dilution infection technique and calculation by the Reed and Muench method.

A cytotoxicity test and a coronavirus quantification test are made after a 24 h incubation. The cytotoxicity of the different compounds is determined at each test on a plate of non-infected cells by a viability test (MTS Test, Promega). This test is based on the measurement of the metabolic activity of cells, which transforms a substrate (MTS tetrazolium) into a product (Formazan), soluble in the medium and the absorbance measured at 490 nm of which proportionally reflects the number of living cells. The ratio of the absorbance in each well to the mean absorbance of the wells of the control cells (not treated by the compounds) is calculated and indicated in the schemes as a cellular viability index (relative cellular viability).

The effect on the in vitro viral production is measured by determining the infectious titres (TCID50/mL) made on VERO-E6 cells, the titres being calculated according to the Reed and Muench technique. The ratio of the infectious titre under each condition has been expressed as a function of the infectious titre measured under the control condition (without treatment).

The results are set out in FIGS. 1A (infectious titres expressed in log 10 TCID50/mL) and 1B (titres expressed in TCID50/mL).

The infectious titres measured under the experimental conditions in the presence of the tested compounds are strongly reduced in comparison with the control condition, where the cells are infected but not treated.

Indeed, monensin (6 µM), berberine (12.5 µM) and apigenin (15 µM) allow for a reduction of 97.8%, 78.4% and 97.8% respectively of the infectious titres with respect to the control (see FIG. 1).

Figure 2:
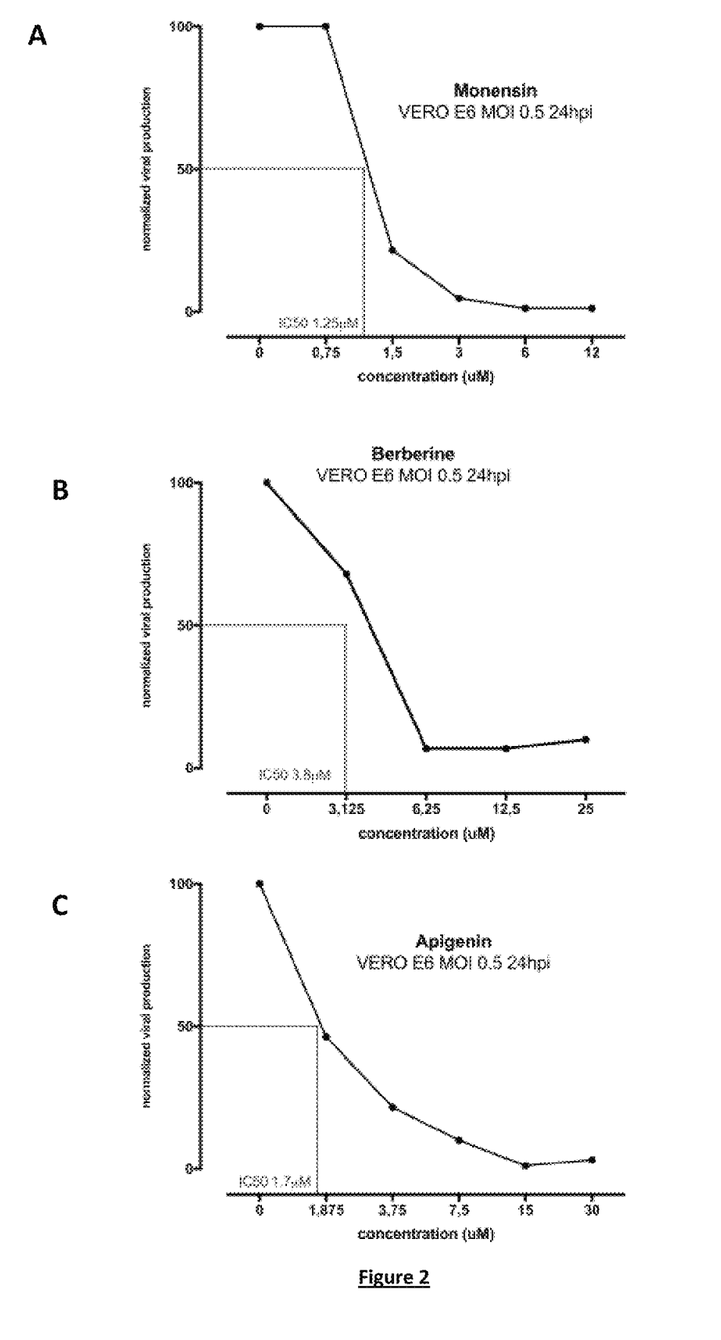
FIG. 2. Measurement of the IC50 (concentration necessary to obtain 50% of normalised viral production) of the tested compounds (A—monensin, B—berberine, C—apigenin) on VeroE6 cells infected by the MERS-CoV coronavirus. The infectious titres have been obtained by the limit dilution infection technique and calculation by the Reed and Muench method.

From these results, a wider concentration range has been tested for each of the three compounds on VeroE6 cells under the same experimental conditions, in order to determine the efficient concentration range, and thus determine an IC50 (half maximal Inhibitory Concentration), namely the dose necessary to obtain a 50% viral production inhibition (see FIG. 2).

It has been possible to determine an IC50 value for these three compounds:

1.25 µM, for monensin
3.8 µM for berberine and
1.7 µM for apigenin.

These IC50 values are relatively low in comparison with usual concentrations known for these compounds in their applications out of the infectious fields. These values are also very far from the cytotoxicity concentrations (CC50).

Figure 3:
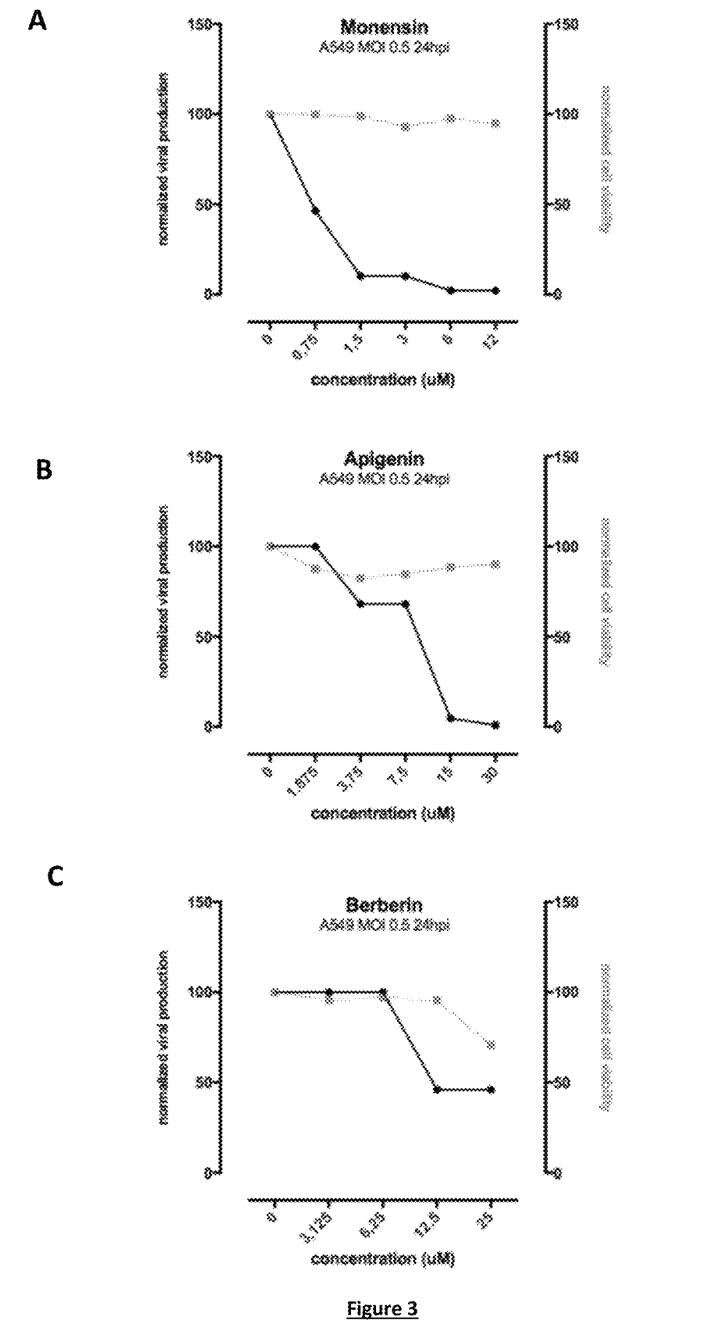
FIG. 3. Measurement of antiviral efficiency of the tested compounds (A—monensin, B—apigenin, C—berberine) on A549 respiratory epithelial human cells infected by the MERS-CoV coronavirus: the infectious titres have been obtained by the limit dilution infection technique and calculation by the Reed and Muench method. The normalised viral production is measured in parallel to the cell viability, as a function of the concentration of the compounds being used.

Similar efficiency results have also been obtained for these three compounds in another premium cellular model, that of the human respiratory epithelial cell line A549 (FIG. 3).

BIBLIOGRAPHY

Patents

FR 2 953 410
FR 3 033 701
FR 3 049 861
WO 2016/013793
WO 2013/185126
US 2009/0149545
WO 2015/157223

Non-Patents

Emmie de Wit, Neeltje van Doremalen, Darryl Falzarano & Vincent J. Munster. *SARS and MERS: recent insights into emerging coronaviruses*. Nature Reviews Microbiology. 14, 523-534 (2016).

R. Dijkman, L. van der Hoek. *Human coronaviruses 229E and NL63: close yet still so far*. J Formos Med Assoc 108 (2009), pp. 270-279

Dyall J, Coleman C M, Hart B J, Venkataraman T, Holbrook M R, Kindrachuk J, Johnson R F, Olinger G G Jr, Jahrling P B, Laidlaw M, Johansen L M, Lear-Rooney C M, Glass P J, Hensley L E, Frieman M B. *Repurposing of clinically developed drugs for treatment of Middle East respiratory syndrome coronavirus infection*. Antimicrob Agents Chemother. 2014 August; 58(8): 4885-93.

Jaffar A. Al-Tawfiq et al., *Ribavirin and Interferon Therapy in Patients Infected with the Middle East Respiratory Syndrome Coronavirus: An Observational Study*. International Journal of Infectious Diseases: IJID: Official Publication of the International Society for Infectious Diseases 20 (March 2014): 42-46

Josset L, Menachery V D, Gralinski L E, Agnihothram S, Sova P, Carter V S, Yount B L, Graham R L, Baric R S, Katze M G. *Cell host response to infection with novel human coronavirus EMC predicts potential antivirals and important differences with SARS coronavirus*. MBio. 2013 Apr. 30; 4

Adedeji A O, Sarafianos S G. *Antiviral drugs specific for coronaviruses in preclinical development*. Curr Opin Virol. 2014 October; 8: 45-53.

Kilianski A, Baker S C. *Cell-based antiviral screening against coronaviruses: developing virus-specific and broad-spectrum inhibitors*. Antiviral Res. 2014 January; 101: 105-12.

Shibata C, Ohno M, Otsuka M, Kishikawa T, Goto K, Muroyama R, Kato N, Yoshikawa T, Takata A, Koike K. *The flavonoid apigenin inhibits hepatitis C virus replication by decreasing mature microRNA122 levels*. Virology. 2014 August; 462-463: 42-8.

Lv X, Qiu M, Chen D, Zheng N, Jin Y, Wu Z. *Apigenin inhibits enterovirus 71 replication through suppressing viral IRES activity and modulating cellular JNK pathway*. Antiviral Res. 2014 Jun. 24; 109C: 30-41.)

Song S, Qiu M, Chu Y, Chen D, Wang X, Su A, Wu Z. *Berberine down-regulates cellular JNK and NF-κB activation and this may result in an inhibition of HSV replication*. Antimicrob Agents Chemother. 2014 Jun. 9.

Wu Y, Li J Q, Kim Y J, Wu J, Wang Q, Hao Y. *In vivo and in vitro antiviral effects of berberine on influenza virus*. Chin J Integr Med. 2011 June; 17(6): 444-52.

The invention claimed is:

1. A method for treating a MERS-CoV (Middle-East Respiratory Syndrome) coronavirus infection of a human being or an animal comprising the administration to said human being or animal of a pharmaceutical or veterinary composition comprising, in a suitable pharmaceutical vehicle, at least one compound chosen from Apigenin and Berberine.

2. The method of claim 1, wherein the pharmaceutical or veterinary composition comprises Apigenin.

3. The method of claim 1, wherein the pharmaceutical or veterinary composition comprises Berberine.

4. The method of claim 2, wherein the pharmaceutical or veterinary composition comprises one of the following combinations:
Apigenin and Berberine;
Apigenin and Monensin; or
Apigenin, Berberine and Monensin.

5. The method of claim 1, comprising an antiviral agent chosen from the group consisting of a protease inhibitor, a helicase inhibitor, and a MERS-CoV virus cell entry inhibitor.

6. The method of claim 1, comprising an antiviral agent chosen from the group consisting of ribavirin and an interferon.

7. The method of claim 6, wherein the interferon is interferon alpha-2b.

8. The method of claim 1, wherein the pharmaceutical or veterinary composition is in a dosage form intended for administration by inhalation.

* * * * *